US006557298B2

(12) United States Patent
Obert et al.

(10) Patent No.: US 6,557,298 B2
(45) Date of Patent: May 6, 2003

(54) TREATMENT OF SEEDS WITH COATINGS CONTAINING HYDROGEL

(75) Inventors: Janet C. Obert, Crestwood, MO (US); Frank C. Kohn, St. Louis, MO (US); Deborah L. Neumann (nee Terrian), Carmel, IN (US); Jawed Asrar, Chesterfield, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/950,470

(22) Filed: Sep. 10, 2001

(65) Prior Publication Data

US 2002/0095864 A1 Jul. 25, 2002

Related U.S. Application Data

(60) Provisional application No. 60/232,694, filed on Sep. 15, 2000.

(51) Int. Cl.[7] ................................................ A01C 1/06
(52) U.S. Cl. ........................................................ 47/57.6
(58) Field of Search ........................................... 47/57.6

(56) References Cited

U.S. PATENT DOCUMENTS

| | | | | |
|---|---|---|---|---|
| 3,911,183 A | | 10/1975 | Hinkes .......................... 428/15 |
| 4,249,343 A | * | 2/1981 | Dannelly ..................... 47/57.6 |
| 4,250,660 A | * | 2/1981 | Kitamura et al. ............. 47/57.6 |
| 4,258,179 A | * | 3/1981 | Kawata et al. ................. 536/95 |
| 4,465,017 A | * | 8/1984 | Simmons ..................... 118/418 |
| 4,715,143 A | | 12/1987 | Redenbaugh et al. ......... 47/57.6 |
| 4,779,376 A | | 10/1988 | Redenbaugh ................ 47/57.6 |
| 4,780,987 A | | 11/1988 | Nelsen et al. ................ 47/57.6 |
| 4,808,430 A | | 2/1989 | Kouno ............................ 427/4 |
| 4,985,062 A | * | 1/1991 | Hughes ........................... 71/77 |
| 5,080,925 A | | 1/1992 | Kouno ............................ 427/4 |
| 5,106,648 A | | 4/1992 | Williams ........................ 427/3 |
| 5,221,313 A | | 6/1993 | Mortvedt et al. ............... 71/63 |
| 5,328,942 A | * | 7/1994 | Akhtar et al. ................. 524/35 |
| 5,572,827 A | | 11/1996 | Conrad ......................... 47/57.6 |
| 5,632,799 A | | 5/1997 | Behel, Jr. et al. ............... 71/63 |
| 5,701,699 A | | 12/1997 | Carlson et al. ............... 47/57.6 |
| 5,706,602 A | | 1/1998 | Kohno et al. ................. 47/57.6 |
| 5,787,640 A | | 8/1998 | Duke ........................... 47/57.6 |
| 5,791,084 A | | 8/1998 | Kohno et al. ................. 47/57.6 |
| 5,910,281 A | | 6/1999 | Kohno et al. ................. 264/343 |
| 5,930,949 A | | 8/1999 | Tsujimoto et al. ............ 47/57.6 |
| 5,939,356 A | | 8/1999 | Wellinghoff ................ 504/100 |
| 5,950,360 A | | 9/1999 | Heinrich et al. .............. 47/58.1 |
| 6,199,318 B1 | * | 3/2001 | Stewart et al. ................ 47/57.6 |

FOREIGN PATENT DOCUMENTS

| | | | | |
|---|---|---|---|---|
| DE | 4417555 | | 11/1995 | .......... A01N/25/04 |
| WO | WO 85/01736 | | 4/1985 | ........... C08L/33/26 |
| WO | WO 00/25568 | | 5/2000 | ............ A01C/1/06 |

OTHER PUBLICATIONS

International Search Report for Application No. PCT/US01/42127 dated Apr. 9, 2002.
Abstract XP-002193915, A. Mittnacht, 122:207665, New Insecticides for the Coating of Beet Seeds.
Abstract XP-002193916, J. Mugnier, 120:263687, Triticonazole Seed Fungicide for Cereals.
Abstract XP-002193917, R.E. Beale, 131:195711, A Unique Fungicide for the Control of Take-All in Wheat.
Abstract XP-002193918, Yazaki Corp., Gel Coating Seed Storage Properties Obtain Coating Seed Aqueous Gel Pore Freeze Dry Obtain Product.
Abstract XP-002193919, Asada Shoji KK, New Coating Seed Afforestation Fine Powder Seed Coating Agent Compose Pagodite Silicate Powder Polymer Absorb Adhesive Agent Germinate Accelerate.
Abstract XP-002193920, Yazaki Corp., The Method Includes (a) Coat-Processing Seeds with the Hydrogel Containing Water Absorbing Polymer and (b) Drying Prepared Gel Coated Seeds.
Abstract XP-002193921, Asano H., Pulverise Coating Seed Obtain Pulverise Coating Water Repel Agent Fine Powder High Water Absorb Polymer.
Erisorb-Improving Soil Water Holding Capacity; http://www.eridan-asia.com/pages/erisorb.html; May 3, 2000.
Patent Abstract entitled: Alginate Hydrogel Microspheres and Microcapsules Prepared by Spinning Disk Atomization; PolymerLaboratory, Swiss Federal Institute of Technology Lausanne; Oct. 3, 1999; Biotechnology & Bioengineering, vol. 67, No. 5, Mar. 5, 2000; pp. 616-622.

* cited by examiner

*Primary Examiner*—Charles T. Jordan
*Assistant Examiner*—Bret Hayes
(74) *Attorney, Agent, or Firm*—Nelson Mullins Riley & Scarborough, LLP

(57) ABSTRACT

Methods for treating seeds and improving the uptake by plants of active ingredients with which seeds are treated. Seeds are coated with dry mixtures of hydrogel and active ingredients that produce desirable effects on the seed, a plant that may emerge from the seed or both.

20 Claims, No Drawings

TREATMENT OF SEEDS WITH COATINGS CONTAINING HYDROGEL

This Application claims the benefit of U.S. Provisional Application No. 60/232,694, filed Sep. 15, 2000.

BACKGROUND OF THE INVENTION (1) Field of the Invention

The present invention relates to treatment of seeds with fungicides, pesticides, chemical hybridizing agents and other chemical agents, and more particularly to such treatment for enhancing the uptake of such agents into the plants that emerge from the seeds.

(2) Description of the Prior Art

Growing crops and other plants have long been treated with a variety of active chemical agents to impart to the plants desirable effects, such as enhanced growth characteristics or enhanced resistance to pests or diseases. Examples of such agents include herbicides, fungicides, insecticides, chemical hybridizing agents, auxins, and plant growth regulators.

Active chemical agents have been applied by application of the agents to the plants themselves and to the growing medium (e.g., soil) for the plants. However, it has been found that treatments can be employed prior to the emergence of the plants, by applying active chemical agents in a manner to affect the seeds, either by applying the agents to the growing medium near the seeds or, more preferably, by applying the agents directly to the seeds themselves. In particular, it has been discovered that if the active chemical agents are applied to the seeds prior to or during germination of the plants, or to the growing medium in which the seeds are planted, the agents may be taken up into the resulting plants via the seed or root, thereby producing the desired effect in the resulting plants themselves.

For several reasons, such pre-emergent application often has been found advantageous relative to post-emergent topical application to the plants. For example, application of the active chemical agents to the seeds prior to or during germination of the plants, or to the growing medium in which the seeds are planted, has been found to eliminate the need for the expensive equipment required for topical application of such agents to in situ growing plants, to reduce the waste associated with the topical application to in situ growing plants, to reduce the run-off associated with such topical applications and the resulting need for repeated re-application of the agents.

On the other hand, pre-emergent techniques also suffer certain drawbacks as well. For instance, whether the active agent is applied to the growing medium or directly to the seed prior to planting, the active agent often tends to bond in some fashion to the soil (or other growing medium) or certain components of the soil. This can limit uptake into the plant or otherwise inhibit delivery of an effective dose to the pest or target site in the plant. In addition, applying the active agent to the soil in which the seeds are planted, such as by applying the agent in a band over the soil in which the seeds are planted, requires additional costs, efforts and equipment associated with in situ applications and results in run-off and so loss of some of the agent and increase of environmental concerns.

Applying the active agent to the seed itself is fraught with other problems as well. First, it is usually difficult to bond active agents to seeds. And once the active agent is bonded to the seed, such as by use of an adhesive, the method of adherence, or active agent itself can cause agglomeration of seeds together, making it difficult to use standard planting equipment, and wasting seed and active agent as masses of agglomerated seeds and active agent are planted instead of individually coated seeds. Moreover, once adhered, much of the active agent is typically lost due to abrasion encountered during handling. In addition, whether it is because of the above-mentioned tendency of active agents to bond with soil or soil-components or for some other reason, conventional seed coating techniques do not effectively counter the low rates of consequent uptake of the agent into the resulting plants. Indeed, whether the active agent has been added to the soil or directly to the seed, the active agent concentration in the plants resulting from the pre-emergent applications can be significantly lower than that resulting from the post-emergent topical applications. Therefore, even pre-emergent application techniques have required undesirably high dosage rates, re-treatment of plants at a later stage of development, or both.

There have been reports of attempts to treat seeds with certain active agents by coating the seeds in a water-saturated hydrogel containing the agents. Such techniques entail their own problems, primarily involved not only with the space considerations resulting from the relatively large seed coatings, but also with the difficulty in adhering the water-saturated hydrogel to the seed, in keeping the coating congealed together, in handling such gelatinous masses in place of discrete, solid seeds, with agglomeration together of coated seeds and with the undesirable effects of keeping the seeds moist (e.g., germination or spoilage), especially during storage. Thus, techniques for dealing with some of these problems have been proposed. For example, certain U.S. patents have suggested placing each seed in a gelatinous mass, or even in a bubble within the gelatinous mass, and/or exposing the seed-containing globules of gelatinous mass to certain metal ions to cross-link the hydrogel along the outer surface of the gelatinous globule about the seed to form a solid coating over the globule, encasing the water-saturated hydrogel. However, such efforts have not proved satisfactory because they still do not address all of the problems discussed above (e.g., the seed being encased in an undesirably large coating, resulting in additional storage and transportation costs as well as difficulties in using standard equipment for distributing the seeds, the presence of moisture, not to mention the question of efficacy in imparting appropriate active agent concentrations in the resulting plants, and the potential undesirable effects of the hardened outer casing) and because of the additional efforts and expense they involve.

Accordingly, there has been a continual search for seed treatment techniques that maintain satisfactory transportation, storage, and handling properties of the seeds, yet produce acceptable levels of active agents in the resulting plants.

SUMMARY OF THE INVENTION

The present invention, therefore, is directed to a novel method for treating a seed, comprising forming on the seed a coating comprising a dry mixture of hydrogel and an active ingredient for producing a desirable effect on the seed, a plant that may emerge from the seed or both.

The present invention is also directed to a method for improving delivery of an active ingredient to a plant grown from a seed, the active ingredient being one that produces a desirable effect on the plant. The method comprises forming on the seed a coating comprising a dry mixture of hydrogel and the active ingredient, and thereafter planting the seed in a growth medium.

Among the several advantages of this invention, may be noted the provision of a method for coating seeds with active ingredients that enhances uptake of the active ingredients in resulting plants; the provision of such method that provides a relatively abrasion-resistant coating; the provision of such method that avoids the problems associated with moistening the seeds; the provision of such method that is accomplished with a relatively thin coating; the provision of such method that reduces or eliminates the need for re-treatments; the provision of such method improving delivery of an active ingredient to a target site or pest within or in the vicinity of the plant and the provision of a pre-emergent method for treating plants with such advantages.

DETAILED DESCRIPTION OF THE PREFERRED EMBODIMENTS

In accordance with the present invention, it has been discovered that seeds coated with a dry mixture of hydrogel and an active ingredient for producing a desirable effect on the seed, a plant that may emerge from the seed, or both, resists loss of coating due to abrasion encountered during handling, storage, transportation, distribution and sowing, and also provides long lasting treatment of the seed with that effect and even, if so desired, provides such treatment to the plant that later emerges from the seed. In fact, surprisingly, the seed coating of this invention has been found to increase the uptake of the active ingredient in the resulting plant, permitting use of lower dosages of active ingredients, and to maintain an effective concentration of the active ingredient throughout the period from planting to germination, which can last a week or two, and even through the life of the later emerging plant or at least until harvesting, which can extend another several weeks or more. It is believed that these improvements in uptake and duration of efficacy are at least in part because the seed coating of this invention seems to inhibit the bonding of active ingredients to the growing medium (e.g., soil) or a component thereof that has plagued various prior art treatment techniques. These improvements in uptake and duration of efficacy may also be at least due in part to the an interaction between the hydrogel and the active ingredient where the movement of the active ingredient is increased in an aqueous phase, thereby resulting in greater uptake of the active material into the plant via the seed or root.

In any event, however, compared to prior art seed or soil treatment techniques, the seed coatings of this invention increases the uptake of active ingredients into resulting plants and in a sense control the release of the active ingredient into the plant so as to maintain in the plant a long-lasting high concentration of the active ingredient. Thus, a single pre-planting seed treatment of this invention can provide long-term treatment of the seed, as well as post-emergent treatment of the plant, without the need for re-treatment, even in situ re-treatment, such as expensive and cumbersome treatment of crops in the field.

Therefore, the present invention results in savings of the efforts, costs and drawbacks of such re-treatment, including those associated with the equipment for the re-treatment (particularly the elaborate equipment that can be required for re-treatment in the field), the re-treatment processes themselves, and the wasteful excess of active ingredient resulting from run-off, evaporation, imprecise application, and so forth. Avoiding the wasteful excess of active ingredient also reduces the risk of potential environmental problems arising from run-off of the excess active ingredient.

Moreover, the dry seed coatings of the present invention further provide several advantages over the wet coatings reported in the prior art. For example, the coating is so thin and light as to avoid significant transportation, handling and storage difficulties and costs, as well as to avoid the need for new or customized equipment to handle larger seed units. Moreover, the seeds bearing the dry coatings of this invention do not require further treatments to encase the coating, as has been the case with gelatinous water-saturated hydrogel coatings described in the prior art. In addition, the dry coatings of the present invention avoid the spoilage and premature germination problems associated with use of high water contents.

The seeds and plants with which the present invention is useful can be of any species. However, they are preferably plant species that are agronomically important. Of particular importance are corn, peanut, canola/rapeseed, soybean, curcubits, crucifers, cotton, rice, sorghum, sugar beet, wheat, barley, rye, sunflower, tomato, sugarcane, tobacco, oats, as well as other vegetable and leaf crops. The subject formulation is particularly useful on the seeds or plants of corn, soybeans, wheat, or cotton.

In one embodiment of the invention, the seed or plant is transgenic. The transgenic seed or plant on which the present invention is useful is engineered to express a desirable characteristic and, in particular, to have at least one heterologous gene encoding for the expression of a protein that is pesticidally active and, in particular, has insecticidal activity. The heterologous gene in the transgenic seeds and plants of the present invention can be derived from a microorganism such as Bacillus, Rhizobium, Pseudomonas, Serratia, Trichoderma, Clavibacter, Glomus, Gliocladium and mycorrhizal fungi. In particular, it is believed that the present method would be especially beneficial when the heterologous gene is one that is derived from a Bacillus sp. microorganism and the protein is active against corn root worm. It is also believed that the present method would be especially beneficial when the heterologous gene is one that is derived from a Bacillus sp. microorganism and the protein is active against European corn borer. A preferred Bacillus sp. microorganism is *Bacillus thuringiensis*.

As noted above, the coating for the seed is a mixture of an active ingredient in a hydrogel. There may be some instances in which the precise identity of the type of the active ingredient is significant to the present invention. For instance, the present invention may provide an additional advantage with respect to a particular type of active ingredient over prior art application techniques or may provide an additional advantage with respect to certain active ingredients beyond those provided with respect to other active ingredients. However, the present invention is in the mechanism of application of active ingredients in general by incorporating them in a dry seed coating with a hydrogel. Therefore, in general, the precise identity and nature of the active ingredient is not important to the concept of this invention and so the nature or identity of the active ingredient should not be viewed as limiting in the scope of the present invention. In most cases, it is important only that the active ingredient be one that is designed to impart to the seed, plant or both a desired effect.

Nevertheless, although this invention is not limited by the type of active agent in terms of what effect the agent is desired to produce, it is preferred that the active agent be a solid, especially a solid that may be granulated for dispersal throughout the coating, although liquids that are so dispersible and capable of being retained in the coating at desirable concentrations may be used as well. Examples of so retaining or dispersing liquids throughout a hydrogel matrix include agitating the liquid to form small globules that may then be dispersed throughout a solid hydrogel matrix, and encasing such small globules of liquid active agent in a solid shell and then dispersing the encased globules throughout a solid hydrogel matrix Active ingredients that can be employed in the coatings of the present invention may be any agent, preferably a chemical agent, that produces a desired effect on the seed, the plant that ultimately emerges from the seed, or both. Non-limiting examples of such chemical agents include pesticides (such as fungicides, acaricides, miticides, insecticides, insect repellants, bird repellants, rodenticides, molluscicides, nematicides, bactericides, and fumigants), herbicides, chemical hybridizing agents, auxins, antibiotics and other drugs, biological attractants, growth regulators, pheromones and dyes. Specific non-limiting examples of chemical agents useful as active ingredients include triticonazole, imidacloprid, tefluthrin, and silthiophenamide (N-allyl-4,5-dimethyl-2-trimethylsilylthiophene-3-caboxamide).

In its broadest sense, the term "active ingredient" as used herein also includes non-chemical agents, even microorganisms, and basic growth aids, such as fertilizers, nutrients, and energy sources (e.g., sugars and other carbohydrates and ATP). Further examples of such types of agents, and examples of specific agents themselves may be noted in U.S. Pat. No. 4,779,376 to Redenbaugh, incorporated herein by reference. The active ingredient may consist of a single type of active agent, or the active ingredient may consist of a combination of active agents.

In a further embodiment of the present invention, such active agents can be incorporated into a controlled released formulation. Although such formulations are referred to as "controlled" release, the term "controlled" is not meant to imply that the release of agent is managed continuously and it is not necessary that the formulations regulate the release with any particular precision. By "controlled release formulation" what is meant is simply that incorporating the active agent into such formulation delays the release of the active agent into the surrounding environment and/or reduces the rate of release of the active agent into the surrounding environment. The controlled release formulation typically would employ an agent that impedes release of the active ingredient into the surrounding environment, thereby delaying the release or reducing the rate of release. Many such agents and techniques are well known in the art. For example, controlled release formulations are disclosed in McFarlane et al., *Pesticide Science,* 9:411–424 (1978); in *Controlled Delivery of Crop-Protection Agents,* R. M. Wilkins, Ed., Taylor & Francis, London (1990); and *Controlled-Release Delivery Systems for Pesticides,* H. B. Scher, Ed., Marcel Dekker, Inc., New York, (1999).

In the present invention, controlled release techniques may be employed in any of several ways (or in a combination of such ways). For instance, coated seeds of this invention may be encapsulated in a controlled release formulation, or the particles of active agent distributed through the hydrogel in the coating may be coated with a controlled release formulation, or the active agent may be mixed with the controlled release agent, or the controlled release agent may be dispersed through the coating. Any of these techniques may be used alone or in combination to enhance even further the controlled (i.e., delayed) release provided by either the controlled release formulation itself or the controlled release detected with the present invention even without such formulation.

In short, the active ingredient is simply any ingredient produces an effect on the seed or the plant that emerges from the seed, or on both the seed and the plant. The ingredient is applied to the seed because that effect is desired to produce in the seed, plant or both. Typically, the desired effect is one that is beneficial to the seed or plant. Thus, it is contemplated that essentially any effect on the seed or plant would be desired under some circumstances and so is contemplated within the scope of the present invention.

Non-limiting examples of such desired or desirable effects include increased protection from, resistance to or counteraction to pests (such as mites or other acarids, fungi, bacteria, insects, birds, mollusks, rodents, and nematodes), disease, herbicides or other potentially phyto-toxic chemicals, increased weather tolerance, or improved size, quantity, taste, scent, appearance, texture, growth rate, or harvesting, shipping, storage or handling qualities of the seeds, plants or seeds, fruits or vegetables borne by the plants. Although reference is made herein at times to imparting the desired effect to the seed or plant, it should be understood that such language is used in a broad sense in that the effect need not be a characteristic of the seed or plant itself, but may be the result of the proximity of the active ingredient to the seed or plant. For example, increased pest resistance of a coated seed may be the result of a protective barrier associated with the coating rather than a change in the internal chemistry or biology of the seed. Yet, for the purposes of this disclosure, the seed is considered to have been imparted with the desired effect of pest resistance.

The hydrogel used in the coating of the present invention is a cross-linked polymer that swells without dissolving in the presence of water, absorbing at least 10 times its weight in water. It is believed that any hydrogel can be effective in the present invention, in view of the application in the environment, it is desirable that the hydrogel be one that is not an environmental pollutant. While the hydrogel may be a natural or a synthetic hydrogel, synthetic hydrogels have can be particularly advantageous in terms of water absorptivity and shelf life. Synthetic hydrogels are usually cross-linked polyacrylamides or cross-linked polyacrylates and have been reported to remain active for up to two years or more. Other examples of suitable hydrogels include those of carrageenan, agar and alginic acid, and gellan gum. Further examples of hydrogels may be noted in U.S. Pat. No. 4,779,376 to Redenbaugh, incorporated herein by reference, and in commonly available references on hydrogels. In short, hydrogels, as the term is used herein, are super absorbent polymers capable of absorbing from 10 to over 100, such as 50 or even 80 to over 100, times their weight in water. Some hydrogels are able to absorb as much as 400 to 500 times their weight in water; others as much as 1,500 times their weight in water. In particular, Aridall Superabsorbent Polymer (potassium polyacrylate) and Aqualon Aquasorb (sodium carboxymethylcellulose) have been found suitable for use in the present invention.

As noted above, the seed coating of the present invention is dry. As used herein, "dry" refers to water content. It should be recognized, however, that "dry" is a relative term in that it is difficult if not impossible to maintain a mixture containing such hydrophilic material as a hydrogel 100% water-free. Thus, recognizing such constraints, as used herein, the term "dry" means that the material that is dry is not gelatinous or tacky, but has the appearance and feel of a solid. Quantitatively, "dry", as used herein, means a water content of less than 4% of the saturation water content of the hydrogel, the saturation water content being the maximum amount of water the hydrogel in the mixture in question can absorb at ambient temperature and pressure. Thus, for instance, a dry coating containing a hydrogel that can absorb 100 times its weight in water has a water content of less than 4 times the weight of the hydrogel. Preferably, however, the water content of the dry coatings of the present invention is less than that of the hydrogel content, by weight. More preferably, the water content of the dry coating is less than about 10% by weight of the coating, even more preferably, less than about 1% by weight of the coating. The water content referred to herein relates to the free water in the hydrogel such that if, for example, the active ingredient is distributed throughout the hydrogel in the form of encapsulated globules of aqueous mixture of active ingredient, the water within the encapsulations is not considered in determining the water content of the coating.

A variety of techniques for applying coatings to seeds are known in the art and may be used for coating the seeds of this invention, provided that the resulting coating is dry as defined above. Thus, those of ordinary skill in the art, upon reading this disclosure, will readily recognize certain techniques that may be employed. Among the coating techniques that may be used may be noted, but are not limited to, mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as SEPIRET (Seppic, Inc., Fairfield, N.J.) and OPACOAT (Berwind Pharm. Services, Westpoint, Pa.).

The formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

Generally, however, the techniques fall into either of two classes, one in which a high water content mixture of hydrogel and active ingredient is added to the seed and then water is removed (referred to herein as the wet process), and the other in which a relatively dry mixture of hydrogel and active ingredient is applied to the seed (referred to herein as the dry process).

An initial step according to the wet process, is preparation of a wet mixture of hydrogel and active ingredient. The wet mixture may be prepared in any of several ways. For example, the active ingredient, which (as explained above) may be a single active agent or a combination of active agents, may be mixed with water to form an aqueous solution and then the hydrogel may be mixed into the aqueous solution. Alternatively, the active ingredient may be mixed with the hydrogel or otherwise added to the water simultaneously with the hydrogel. Or, the hydrogel may be mixed with the water, followed by addition of the active ingredient to the aqueous hydrogel mixture. If the active ingredient consists of more than one agent, the various agents can be combined to form a mixture that is added to the water or to the aqueous hydrogel mixture or the various agents can be combined with the water or aqueous hydrogel mixture without mixing them together first. Or else, if so desired, the various agents can be added at various stages during the preparation of the wet mixture.

While the particular water concentration of the wet mixture is not crucial, higher water concentrations mean more water must be removed later to produce a dry coating. Therefore, lower water concentrations are preferred, and generally only enough water to reduce the viscosity to a level to allow convenient handling is used.

Other additives, such as fillers (e.g., diatomaceous earth, calcium carbonate, or silica) may be incorporated into the wet mixture as well. The wet mixture may be applied to seeds by any standard techniques for applying liquids to seeds. For example, the coating process can comprise spraying a composition comprising the formulation onto the seed while agitating the seed in an appropriate piece of equipment such as a tumbler or a pan granulator.

The wet mixture may then be applied to the seed or seeds by conventional seed-coating techniques. For example, the coating process can comprise spraying a composition comprising the formulation onto the seed while agitating the seed in an appropriate piece of equipment such as a tumbler or a pan granulator.

In one embodiment, when coating seed on a large scale (for example a commercial scale), typically seed is introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the active ingredient in the controlled release formulation, the desired concentration on the finished seed, and the like. The treatment composition can be applied to the seed by a variety of means, for example by a spray nozzle or revolving disc. The amount of liquid is typically determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry. In another embodiment, seeds can also be coated by placing the known amount of seed into a narrow neck bottle or receptacle with a lid. While tumbling, the desired amount of seed treatment composition can be added to the receptacle. The seed is tumbled until it is coated with the seed treatment composition. After coating, the seed can optionally be dried, for example on a tray.

The wet mixture coating may then be dried by conventional methods. For example, a desiccant or mild heat (such as below about 40° C.) may be employed to produce a dry coating. The water content of the dry coating will be discussed below.

The alternative coating technique, the dry method, also involves two steps. The first step involves application of a "sticking agent" as an adhesive film over the seed so that the hydrogel/active ingredient mixture in the form of a powder can be bonded to the seed to form the coating of this invention. The film may be a thin coating of wet hydrogel, with or without active ingredient. Alternatively, a quantity of seed can be mixed with a sticking agent, such as polyethylene glycol, and optionally agitated to encourage uniform coating of the seed with the sticking agent. In the second step, the seed coated with the sticking agent can then be mixed with the powdered mixture of hydrogel and active agent. The dry formulation of hydrogel and active ingredient may contain other additives as discussed above with respect to the wet mixture. The seed and powdered hydrogel and active ingredient mixture can be agitated, for example by tumbling, to encourage contact of the sticking agent with the powdered material, thereby causing the powdered material to stick to the seed.

The present invention contemplates the application to a seed of a dry coating comprising a hydrogel and active agents. The relative proportions of the hydrogel and active agents and the thickness of the coating are not critical to this concept and are within the discretion of the operator. However, it is recognized that the present invention affords certain advantages with respect to such considerations, including the ability to achieve desired effects with lower amounts of active agents than employed in conventional treatments, and the ability to employ thinner coatings than the prior art high water content coatings. Therefore, the following discussion with respect to relative proportions and coating thicknesses is offered for general guidance, but should not be viewed as essential to an understanding of the present invention.

The amount of active ingredient relative to the hydrogel depends on the concentration of active ingredient that is desired to be added to the seed and to be taken up into the plant, which in turn varies widely based on many factors, including the identity of the active ingredient, the type of seed/plant to be treated, the conditions of the growth medium and the watering conditions. As with conventional processes, the range of appropriate concentrations of active ingredient can be quite large. However, typical dosage rates under particular circumstances will be readily apparent to those of ordinary skill in the art based on the concentration of active ingredient conventionally desired about the seed, in the rhizosphere of the plant or within the plant under the circumstances, but recognizing that the increased uptake associated with employment of the technique of the present invention may allow use of a lower dosage rate of the active ingredient than used in the conventional method.

It will be appreciated that the active ingredient dosage afforded by the present method depends not only on the concentration of the active ingredient in the coating, but also on the thickness of the coating applied to the seed. Of course, a minimum dosage rate is necessary for the active ingredient to affect the seed and/or plant, but because the dosage of the active ingredient is dependent on the combination of the concentration of the active ingredient in the coating as well as the total amount of coating present, a thick coating can compensate for a low active ingredient concentration. Moreover, it has been found that uptake increases with increasing levels of hydrogel. Therefore, the active ingredient concentration can be quite high, compensated for by a thin coating. In any event, however, because the hydrogel absorbs so much water, relatively little hydrogel is needed to produce a substantial effect. Thus, even though a very broad range of relative proportions of hydrogel to active ingredient that can be employed in the present invention and coordinated with a wide range of coating thicknesses, the proportion of active ingredient to hydrogel would typically be quite high even though the range of proportions would be quite broad. It is contemplated that even the preferred range of the active ingredient to hydrogel weight ratio may be anywhere from, say 100 to perhaps 10,000. Generally, however, relatively thin coatings are desired, especially of less than, say, about one millimeter, or even less than about 0.5 millimeters, and so active ingredient concentrations may be set accordingly.

In other words, it is within the control and discretion of the personnel employing the method to coordinate the active ingredient concentration and coating thickness to produce an ultimate desired dosage, which of course will depend on the active ingredient, the type of seed and the environment. Those of ordinary skill in the art will recognize typical ultimate dosages for particular active ingredients, in view of the seeds/plants and environments involved or will readily recognize how such dosages can be easily determined by resort to standard references or standard techniques for determining optimal treatment dosages. Those of ordinary skill in the art then will readily recognize how to coordinate the concentration of active ingredient and coating thickness to achieve the desired dosage (active ingredient concentration in the coating times total amount of coating), taking into account, however, that the increased uptake afforded by the present invention suggests that the desired dosage may be somewhat lower than the conventional dosages. Thus, for example, the operator may coordinate the active ingredient concentration in the coating and the coating thickness to produce an active ingredient dosage of, say, about 100 to about 500 grams per 100 kilograms of seeds, if so desired for that particular active ingredient.

The coated seeds may be handled, transported, stored and distributed in the manner of uncoated seeds. Likewise, they may be sown and watered in the same manner as uncoated seeds as well, using conventional equipment. Typically, the present invention is applicable to crops to be grown in soil, although it may be applied to other plants and growing media without departing from the scope of the invention. It has been found that the seed treatment of the present invention can impart long-lasting desired effects of the active ingredient to the seed and resulting plant without need for re-treatment.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

Three groups of wheat seeds were treated with equal amounts of triticonazole prior to planting. The seeds of the first group were a control group treated with no hydrogel. In addition to the triticonazole, the seeds of the second group were treated with Aqualon Aquasorb. In addition to the triticonazole, the seeds of the third group were treated with Aridall Superabsorbent Polymer. The level of triticonazole in the foliage was measured eighteen days after planting. The levels of triticonazole detected in the foliage were found to be as follows:

| | Triticonazole (ppm) |
|---|---|
| Group 1 | 0.30 |
| Group 2 | 2.05 |
| Group 3 | 1.87 |

EXAMPLE 2

Three groups of wheat seeds were treated with imidacloprid prior to planting. The seeds of the first group were a control group treated with no hydrogel. In addition to the imidacloprid, the seeds of the second group were treated with Aqualon Aquasorb. In addition to the imidacloprid, the seeds of the third group were treated with Aridall Superabsorbent Polymer. The level of imidacloprid in the foliage was measured eighteen days after planting. The levels of imidacloprid detected in the foliage were found to be as follows:

| | Imidacloprid (ppm) |
|---|---|
| Group 1 | 3.13 |
| Group 2 | 13.67 |
| Group 3 | 10.47 |

EXAMPLE 3

Four groups of wheat seeds were treated with radiolabeled (carbon 14) imidacloprid immediately prior to planting. The seeds of the first group were a control group treated with no hydrogel. In addition to the imidacloprid, the seeds of the second group were treated with Aridall Superabsorbent Polymer at a dosage rate of 250 grams per 100 kilograms of seed. In addition to the imidacloprid, the seeds of the third group were treated with Aqualon Aquasorb at a dosage rate of 250 grams per 100 kilograms of seed. In addition to the imidacloprid, the seeds of the fourth group were treated with Aqualon Aquasorb at a dosage rate of 500 grams per 100 kilograms of seed. Forty-three days after planting, the level of imidacloprid in the foliage of the wheat plants was measured. In addition, because some of the imidacloprid may have been converted to other compounds, the level of carbon 14 was measured as an indication of total imidacloprid uptake. The levels of imidacloprid and of carbon 14 detected in the foliage were as follows:

| | Imidacloprid (ppm) | Carbon 14 (ppm) |
|---|---|---|
| Group 1 | 0.29 | 1.30 |
| Group 2 | 0.37 | 1.80 |
| Group 3 | 0.43 | 2.00 |
| Group 4 | 0.70 | 2.50 |

EXAMPLE 4

Six groups of corn kernels were studied. The first group was a control group receiving no special treatment. The second group of corn kernels were planted with the addition of 100 mg of the hydrogel Aqualon Aquasorb B313 per kernel, placed in the bottom of the planting hole approximately 3 cm deep. The third group was treated with just 2 mg of Aqualon Aquasorb per seed, applied as a seed treatment. The fourth group received a seed treatment of 260 grams tefluthrin, a cutworm pesticide, per 100 kilograms of kernels and no hydrogel. The fifth group received a seed treatment of 230 gm tefluthrin/100 kg seed (Raze®) and 2 mg mg Aqualon Aquasorb per kernel (seed treatment). The sixth group received a seed treatment of 230 gm tefluthrin (Raze®) with Aqualon Aquasorb placed in the bottom of the planting hole approximately 3 cm deep in the amount of 100 mg/kernel. With groups 2 and 6, the corn seeds were placed on top of the hydrogel and covered with soil, with the seeds of groups 1, 3, 4, and 5 likewise placed in planting holes and covered with soil. After growth of cornstalks, cutworms were introduced to the stalks at the V1 growth stage and the percentage of stalks destroyed by cutworms was noted for each group at ten days after infestation (DAI), with the following results:

| Treatment | % of Plants Cut 10 DAI |
|---|---|
| Group 1 (Untreated Control) | 100 |
| Group 2 (Untreated Control + 100 mg Aquasorb B313 soil treatment) | 94 |
| Group 3 (Untreated Control + Aquasorb B313 seed treatment) | 100 |
| Group 4 (tefluthrin @ 260 gm ai*/100 kg seed treatment) | 79 |
| Group 5 (tefluthrin @ 230 gm ai*/100 kg seed treatment) + (Aquasorb B313 seed treatment) | 56 |
| Group 6 (tefluthrin @ 230 gm ai*/100 kg seed treatment) + (Aquasorb soil treatment) | 25 |

*ai = active ingredient

EXAMPLE 5

Four groups of corn kernels were studied. The first group was a control group receiving no special treatment. The second group of corn kernels were planted with the addition of 100 mg of the hydrogel Alcosorb AB3S, placed in the bottom of the planting hole approximately 3 cm deep. The third group received a seed treatment of 379 grams tefluthrin (Raze®), a cutworm pesticide, per 100 kilograms of kernels and no hydrogel. The fourth group received a seed treatment of 379 gm tefluthrin (Raze®) with 100 mg Alcosorb AB3S placed in the bottom of the planting hole approximately 3 cm deep.

| Treatment | % of Plants Cut 10 DAI |
|---|---|
| Group 1 (Untreated Control) | 98 |
| Group 2 (Untreated Control + 100 mg Alcosorb AB3S to soil) | 100 |
| Group 3 (tefluthrin @ 379 gm ai*/100 kg) | 69 |
| Group 4 (tefluthrin @ 379 gm ai*/100 kg + 100 mg Alcosorb AB3S to soil) | 54 |

*ai = active ingredient

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed is:

1. A method for treating a seed, comprising forming on the seed a coating comprising a dry mixture of a hydrogel and an active ingredient for producing a desirable effect on the seed, a plant that may emerge from the seed or both, wherein the hydrogel has a saturation water content and the dry mixture has a water content less than about 4% by weight of the saturation water content.

2. A method as set forth in claim 1 wherein the coating is formed on the seed by applying to the seed an additive mixture of the hydrogel and the active ingredient.

3. A method as set forth in claim 2 wherein the additive mixture further comprises water and the method comprises applying the additive mixture to the seed to form a seed coated with a wet mixture of the hydrogel and the active ingredient and then removing water from the wet mixture coating the seed to produce the coating comprising the dry mixture of hydrogel and the active ingredient.

4. A method as set forth in claim 1 wherein the coating has a water concentration less than about 10% by weight.

5. A method as set forth in claim 1 wherein the coating has a water concentration less than about 1% by weight.

6. A method as set forth in claim 1 wherein the active ingredient is at least one active chemical agent.

7. A method as set forth in claim 6 wherein the active ingredient is selected from the group consisting of pesticides, selective herbicides, chemical hybridizing agents, auxins, antibiotics and other drugs, biological attractants, growth regulators, pheromones, dyes and combinations thereof.

8. A method as set forth in claim 6 wherein the chemical agent is selected from the group consisting of triticonazole, imidacloprid, tefluthrin, and silthiophenamide (N-allyl-4,5-dimethyl-2-trimethylsilylthiophene-3-caboxamide).

9. A method as set forth in claim 1 wherein the coating further comprises a controlled release agent.

10. A method as set forth in claim 9 wherein the active ingredient is present in the coating as particles encapsulated in the controlled release agent.

11. A method as set forth in claim 9 wherein the controlled release agent is present in the coating as a formulation encapsulating a layer of the dry mixture, which in turn encapsulates the seed.

12. A method as set forth in claim 9 wherein the coating comprises the active ingredient and the hydrogel distributed throughout the controlled release agent.

13. A method as set forth in claim 1 wherein the active ingredient is one that produces a desirable effect on the plant that may emerge from the seed.

14. A method as set forth in claim 1 wherein the coating is formed on the seed by applying to the seed an adhesive film and then applying to the adhesive coating a dry additive mixture of hydrogel and the active ingredient.

15. A method for improving delivery of an active ingredient to a plant grown from a seed, the active ingredient being one that produces a desirable effect on the plant, the method comprising forming on the seed a coating comprising a dry mixture of hydrogel and the active ingredient, wherein the hydrogel has a saturation water content and the dry mixture has a water content less than about 4% by weight of the saturation water content, and thereafter planting the seed in a growth medium.

16. A method as set forth in claim 15, wherein the coating has a water content less than about 10% by weight.

17. A method as set forth in claim 15, wherein the coating has a water content less than about 1% by weight.

18. A method as set forth in claim 15, wherein the active ingredient is at least one active chemical agent.

19. A method as set forth in claim 15 wherein the active ingredient is selected from the group consisting of pesticides, selective herbicides, chemical hybridizing agents, auxins, antibiotics and other drugs, biological attractants, growth regulators, pheromones, dyes and combinations thereof.

20. A method for improving the delivery of an active ingredient to a plant grown from a seed, the active ingredient being one that produces a desirable effect on the plant, the method comprising depositing a dry mixture of a hydrogel and the active ingredient in a growing medium along with the seed.

* * * * *